United States Patent [19]

Farcasiu et al.

[11] Patent Number: 5,369,214
[45] Date of Patent: Nov. 29, 1994

[54] METHOD FOR SELECTIVE DEHALOGENATION OF HALOGENATED POLYAROMATIC COMPOUNDS

[75] Inventors: Malvina Farcasiu, Pittsburgh; Steven C. Petrosius, Library, both of Pa.

[73] Assignee: The United States of America as represented by the United States Department of Energy, Washington, D.C.

[21] Appl. No.: 180,752

[22] Filed: Jan. 7, 1994

Related U.S. Application Data

[63] Continuation of Ser. No. 33,480, Mar. 18, 1993, abandoned.

[51] Int. Cl.⁵ .......................... C07C 1/20; C07C 22/00
[52] U.S. Cl. .................................... 585/469; 570/204; 570/206; 570/207; 570/208
[58] Field of Search .................... 585/469; 208/145; 570/204, 206, 207, 208

[56] References Cited

U.S. PATENT DOCUMENTS

| | | | |
|---|---|---|---|
| 4,351,978 | 9/1982 | Hatano et al. | 570/204 |
| 4,950,833 | 8/1990 | Hawari et al. | 585/469 |
| 5,141,629 | 8/1992 | Pri-Bar | 585/469 |

FOREIGN PATENT DOCUMENTS 1006386  9/1965  United Kingdom ................ 570/204

OTHER PUBLICATIONS

Kirk–Othmer Concise Encyclopedia of Chemical Technology, (Grayson, M., Ed.), John Wiley & Sons, Publ., New York, 1985, pp. 271, 654.
Petrosius, S. C.; Drago, R. S. J. Chem. Soc. Chem. Comm., 1992, 344.
Ferrughelli, D. T.; Horvath, I. T. J. Chem. Soc. Chem. Comm., 1992, 806.
Farcasiu, M.; Smith, C. S.; Sylwester, A. P.; Ladner, E. L. Prepr., ACS Div. Fuel Chem., 202rd ACS Nat'l Mtg., 1991, 37, 472.
Farcasiu, J.; Smith, C. S. Energy & Fuels, 1991, 5, 83.
Farcasiu, M.; Smith, C. S.; Hunter, E. A. Proc. 1991 Conf. on Coal Sci., (IEA Coal Research, Ltd., Ed.) Butterworth, Heinemann, Ltd., London, 1991, p. 166.

*Primary Examiner*—Alan Siegel
*Attorney, Agent, or Firm*—Robert J. Fisher; Hugh W. Glenn; William R. Moser

[57] ABSTRACT

A method for dehalogenating halogenated polyaromatic compounds is provided wherein the polyaromatic compounds are mixed with a hydrogen donor solvent and a carbon catalyst in predetermined proportions, the mixture is maintained at a predetermined pressure, and the mixture is heated to a predetermined temperature and for a predetermined time.

15 Claims, No Drawings

5,369,214

METHOD FOR SELECTIVE DEHALOGENATION OF HALOGENATED POLYAROMATIC COMPOUNDS

This is a continuation of application Ser. No. 08/033,480 filed Mar. 18, 1993, now abandoned.

BACKGROUND OF THE INVENTION

1. Field of the Invention

The present invention relates to a method for dehalogenating aromatic compounds, and specifically to a method for selective dehalogenation of condensed polyaromatic, halogenated compounds via reduction reactions in the presence of carbon-based catalysts.

2. Background of the Invention

The recognition of the toxicity and carcinogenic properties of halogenated compounds has led to restrictions on the utilization and disposal of such materials. Condensed polyaromatic compounds, such as 1-chloronaphthalene, have industrial applications as solvents, dyes, flame-retardants, and have also been involved in the manufacture of instrument seals and insecticides. Polychlorinated biphenyls (PCBs) are related materials which have had much publicity due to their persistence and adverse impacts on the environment.

The destruction of these materials has proved costly. Presently, incineration is considered the destruction method of choice, with temperatures of 1000° C. required for adequate detoxification.

As a more economical alternative, catalysts have been employed to convert, under milder conditions, the halogenated compounds to relatively innocuous materials, such as carbon dioxide, water and halogen salts and other halogen-containing inorganic compounds such as acid. However, a disadvantage to this method is the loss of carbon as carbon dioxide, especially if the toxic material is present in a mixture with nontoxic materials that also would be destroyed in the process.

A need exists in the art to detoxify halogenated compounds, both neat and in mixtures, while yielding, as products of the reaction, the corresponding unhalogenated compounds. In this way, the detoxified materials can be reutilized.

SUMMARY OF THE INVENTION

It is an object of the present invention to provide a method for dehalogenating and partially saturating substituted aromatic compounds which overcomes many of the disadvantages of the prior art.

It is another object of the present invention to provide a method to dehalogenate aromatic compounds. A feature of the invention is the utilization of carbon as a catalyst. An advantage of the invention is to provide economical detoxification of toxic materials.

Yet another object of the present invention is to provide a method of hydrogenating substituted aromatic compounds. A feature of the invention is the utilization of hydrogen donors and carbon catalysts in the reaction. An advantage of the invention is the production of partially saturated aromatic materials as an alternative feedstock source.

Still another object of the present invention is to provide a method to dehalogenate halogenated compounds. A feature of the invention is the utilization of carbon molecular sieves and hydrogen donors. An advantage of the invention is the facilitation of dehalogenation reactions at temperatures ranging between approximately 300° C. and 500° C.

Yet another object of the present invention is to provide a method to detoxify mixtures containing halogenated compounds. A feature of the invention is the utilization of carbon molecular sieves and hydrogen donors to facilitate reactions at relatively low temperatures. An advantage of the invention is the detoxification of aromatic compounds to yield intact aromatic compounds.

Briefly, the invention provides for a method for dehalogenating halogenated polyaromatic compounds comprising mixing the polyaromatic compounds with a hydrogen donor solvent and a carbon catalyst in predetermined proportions, maintaining the mixture at a predetermined pressure, and heating the mixture to a predetermined temperature and for a predetermined time.

DETAILED DESCRIPTION OF THE INVENTION

Some engineered carbon materials, called carbon molecular sieves, have extremely high surface areas ($>2000$ m$^2$/g). This high surface area, combined with the already observed adsorption activity of carbons, makes this material a good catalyst to facilitate some gas-phase oxidation reactions, such as alcohol oxidations and the deep oxidation of halogenated hydrocarbons, as reported by one of the inventors. (*J. Chem. Soc. Chem. Comm.* 1992, 344.) Porous carbons have been used as active catalysts for the complete oxidation of halogenated hydrocarbons to $CO_2$ and HCl.

Carbon black and other carbon materials has been found by the inventors to cleave C—C bonds in model compounds, with chemical structure relevant to coal and petroleum residues (*Energy& Fuels*, 1991, 5, 83). For example, a very high selectivity (over 90%) was observed for the cleavage of the bond between a condensed polycyclic aromatic ring and an aliphatic carbon. These reactions occurred at low pressures.

Surprisingly and unexpectedly, the combination of hydrogen donors and carbon catalyst materials facilitate replacement of the halogen of halogenated aromatic compounds with a hydrogen to produce the corresponding unhalogenated compound. Another observed reaction is the hydrogen transfer from the hydrogen donor to the polyaromatic rings to produce partial saturation of the aromatic and haloaromatic material. As reported by Ferrughelli, et al. (*J. Chem. Soc. Chem. Comm.* 1992, 806), such a result was observed for chloroaromatics using a rhodium catalyst system, whereby the hydrodehalogenation was accompanied by hydrogenation to produce partially saturated products in addition to the expected aromatic products. Unlike the invented catalyst system, the rhodium catalyst system is homogeneous, wherein the initial step of the reaction is the hydrogenolysis of the $C_{arene}$—Cl bond followed by hydrogenation of the ring. The use of carbon catalysts also have been observed to facilitate selective dehydroxylation of condensed polyaromatic phenols. Generally, the presence of a hydrogen donor results in producing very clean reactions wherein no heavy products are formed.

In summary, this reducing mechanism allows for the recovery of carbon and hydrogen as intact dehalogenated and dehydroxylated molecules, thus aiding in efforts to recycle waste into useful materials.

Carbon Catalyst Material

The carbon molecular sieve material used in these reactions are commercially available as high surface carbons, i.e., carbon black BP2000 (1400 m$^2$/g) from Cabot, and as carbon fibers, i.e., Ashland ACN-210-20 (1500 m$^2$/g). The success of carbon fibers as a catalyst is particularly noteworthy as these materials are useful when the need arises to shape catalysts to various configurations. The inventors also have developed engineered reactive carbon materials which also serve to catalyze the reduction reaction.

These high surface area materials produce efficient catalytic activity for reduction reactions, even when the weight ratio of substrate to catalyst is low, i.e., approximately 1:0.025. Depending on the surface area of the carbon used, weight ratios of substrate to catalyst can vary significantly, and range from approximately 1:.008 to 1:.2.

Background for Reaction Mechanism

Generally, in the case of dehalogenation and dehydroxylation reactions, the mechanism of the carbon black-catalyzed reactions seems to require hydrogen transfer as the first step. Such a reaction scheme is depicted for 2-hydroxynaphthalene, in scheme 1, below:

stable to either further hydrogenation to the substituted tetralin or dehydrogenation back to the initial reactant. If the first hydrogenated bond is $C_1$-$C_2$, the resulting allylic alcohol, 1,2-dihydro-2-naphthol, is rapidly dehydrated to naphthalene. If the first hydrogenation occurs to the unsubstituted ring in the substrate, the corresponding olefin further hydrogenates to form the observed hydroxy-tetralin. Formation of chlorotetralin and bromotetralin in the reactions of halogenated naphthalenes is a strong indication of a similar mechanism occurring for halogenated substrates.

Other hydroxylated and halogenated substrates were also subjected to the carbon catalyzed reduction reaction outlined above. Generally, these substrates include halogenated phenanthrenes, halogenated biphenyls, halogenated naphthalenes and condensed aromatics. Specifically, these substrates include, but are not limited to bromonaphthalene, chloronaphthalene, bromophenanthrene, chlorophenanthrene, chlorobiphenyl, bromobiphenyl, polybrominated naphthalene, polychorinated naphthalene, polybrominated phenanthrene, polychlorinated phenanthrene, polychlorinated biphenyl, polybrominated biphenyl, and combinations

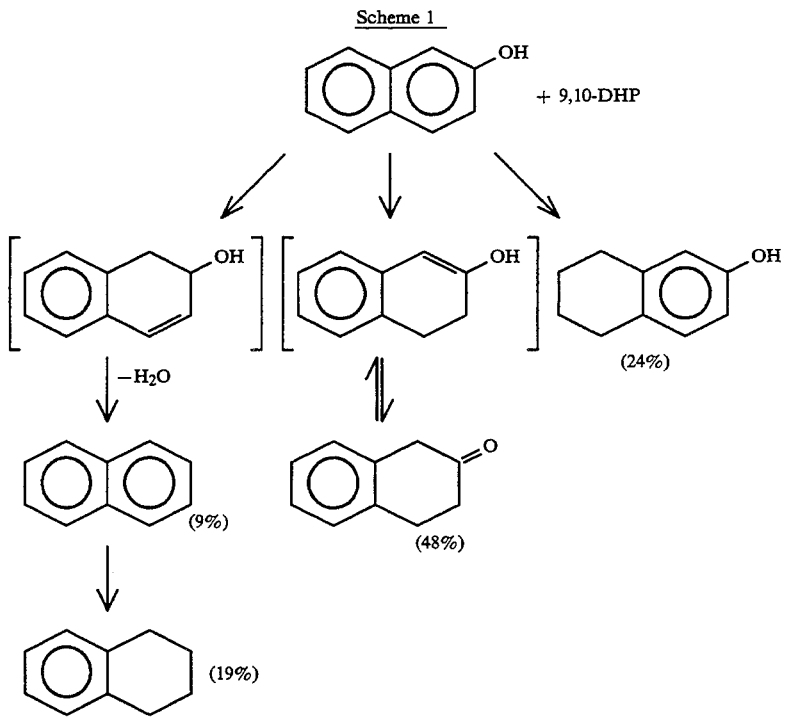

The values for the selectivity of various products specified in scheme 1 are from the reaction at 410° C. and a 4:1:0.1 weight ratio of 9, 10-dihydrophenanthrene (9,10-DHP):2-hydroxynaphthalene:carbon black.

Under the same reaction conditions, the following product distribution was observed for the treatment of 1-chloronaphthalene: 50% naphthalene, 23% tetralin, and 27% chlorotetralin.

The formation of tetralone from 2-hydroxynaphthalene validates reaction scheme 1. The product results from the tautomerization of 3,4-dihydro-2-naphthol which is formed when the first hydrogenated bond is $C_3$-$C_4$. The resulting vinylic alcohol tautomerizes to tetralone before the second hydrogenation can occur. The analogous partially-hydrogenated product forms in the case of chloro- and bromonaphthalene, but is less thereof. A comparison of these reactants is presented in Table 1 below, wherein reactions occurred at 410° C. in the presence of a hydrogen donor, and the weight ratio of donor to substrate to catalyst was 4:1:0.1.

TABLE 1

Hydrodehydroxylation and Hydrodehalogenation of substituted aromatic compounds

| Ar | X | Conversion % w.o. catalyst | Conversion % w. catalyst |
|---|---|---|---|
| (phenanthrene-X) | OH | 20 | 41 |
| | Br | 20 | 95 |
| (naphthalene-X) | Cl | 13 | 39 |
| | Br | 23 | 64 |
| | OH | 7 | 39 |
| (biphenyl with X ortho) | OH | 0 | <1 |
| (biphenyl with X para) | OH | 4 | 4 |
| | Cl | 2 | 5 |

1. All reactions at 410° C., 4:1:0.1 weight ratio of donor to Ar—X to carbon catalyst. Ar—X represents an aryl compound substituted with a moiety designated as X.

Data in Table 1 show that both the degree of dehalogenation and dehydroxylation in various substituted aromatic compounds is substantially increased with an increase in the size of the aromatic system, and is very dependent on the nature of the substituent. For the same aromatic moiety, bromo-substituted aromatics are more reactive than the corresponding chloro derivatives. This halogen-specific reactivity is evident when data for the conversion of 1-chloronaphthalene (depicted in Table 2) is compared with data for the conversion of 1-bromonaphthalene (depicted in Table 3). The data depicted in Tables 2 and 3 compares conversion rates when just a hydrogen donor is used, versus when both a hydrogen donor and a carbon catalyst is used.

The inventors also found that the degree of ring condensation effects the activity of carbon catalyzed reduction reactions. As can be noted in Table 1, reactivity of the catalyzed reactions increases with the increase in the degree of aromatic ring condensation. For the same aromatic compound, the catalyst is more active for the bromo-substituted than the chloro-substituted compounds.

The conversion increases with the increase of catalyst concentration and decreases with the increase of the dilution of the substrate in the reaction mixture.

TABLE 2

Thermal and Catalytic Reactivity of 1-Chloronaphthalene at various temperatures in the presence of 9,10-DHP.[1]

| Temp. °C. | Conversion % Therm. | Conversion % Cat. | Selectivity Tetralin Therm. | Selectivity Tetralin Cat. | Selectivity Naphthalene Therm. | Selectivity Naphthalene Cat. | Selectivity Cl-tetralin Therm. | Selectivity Cl-tetralin Cat. |
|---|---|---|---|---|---|---|---|---|
| 380 | 2 | 23 | 0 | 20 | ~65 | 51 | ~35 | 29 |
| 400 | 6 | 36 | 9 | 20 | 71 | 51 | 20 | 29 |
| 410 | 9 | 39 | 12 | 23 | 65 | 50 | 23 | 27 |
| 430 | 16 | 48 | 10 | 24 | 65 | 50 | 25 | 26 |
| 450[2] | 35 | 65 | 7 | 19 | 53 | 52 | 12 | 15 |

[1]Table 2 reaction conditions: 1 hour, 4:1 weight ratio of 9,10-DHP:substrate. In the catalyzed reactions, the weight ratio of BP2000:substrate is 1:10.
[2]At this reaction temperature, numerous other products are observed.

TABLE 3

Thermal and Catalytic Reactivity of 1-bromonaphthalene at Various Temperatures in the Presence of 9,10-DHP.[1]

| Temp. °C. | Conversion % Therm. | Conversion % Cat. | Selectivity Tetralin Therm. | Selectivity Tetralin Cat. | Selectivity Naphthalene Therm. | Selectivity Naphthalene Cat. | Selectivity Br-tetralin Therm. | Selectivity Br-tetralin Cat. |
|---|---|---|---|---|---|---|---|---|
| 330 | 0 | 12 | 0 | 13 | 0 | 64 | 0 | 23 |
| 350 | 0 | 29 | 0 | 18 | 0 | 52 | 0 | 24 |
| 380 | 6 | 55 | 5 | 30 | 63 | 46 | 33 | 25 |
| 400 | 8 | 68 | 0 | 33 | 63 | 44 | 37 | 24 |
| 410 | 17 | 64 | 6 | 33 | 62 | 40 | 33 | 27 |

[1]Reaction conditions for Table 3: 1 hour, 4:1 weight ratio of 9,10-DHP:substrate. In the catalyzed reaction, a 1:10 weight ratio of carbon to substrate was used.

Reaction Process

The reactions described below in examples 1 through 15 were performed in sealed glass tubes. The substrates, hydrogen donor solvent and catalysts were used in various proportions as described in the examples. Generally, the weight ratio of substrate to H-donor can be selected from the range of approximately 1:.5 to 1:20, with ratios selected from between 1:1–1:4 producing superior results. The weight ratios of substrate to carbon catalyst can also vary, ranging from 1:.008 to 1:.2. A 10% catalyst loading was used in many of the examples, more out of convenience. The following ratios of substituted polyaromatic compounds to hydrogen donor to carbon catalyst produced good results: 1:1:0.025, 1:4:0.1, and 1:10:0.1.

In some instances, an inert internal standard, such as metaxylene, was added so as to monitor the extent of conversion of certain substrates being detoxified while also accounting for the disposition of all reactants and products, i.e., obtaining a good mass balance.

The tubes were heated to predetermined temperatures ranging from approximately 300° C. to 500° C. by placing the tubes in an oven. (Other heating elements can be utilized, including, but not limited to internal heating elements, external heating elements, heated carrier gases, or a combination of these methods.) When temperatures are selected from between approximately 350° C. to 430° C., superior conversion results were obtained. In the examples, heat was applied for one hour. Generally, however, heating times ranging from approximately 10 minutes to 2 hours will yield good results, depending on certain variables. These variables include the weight ratio of the substrates, H-donor and catalyst, the mass transfer of the reactants, and the temperature of the system.

After the reaction, the products were diluted with methylene chloride (if no internal standard was present), filtered over glass wool and magnesium sulfate (anhydrous) and analyzed by gas chromatography and gas chromatography-mass spectroscopy for product identification.

The following examples illustrate the advantages of using carbon molecular sieve catalyst material in conjunction with hydroaromatic hydrogen donors. Hydroaromatic compounds are polycyclic wherein one part of the molecule maintains its aromaticity, thereby allowing, through resonance stabilization, a saturated part of the molecule to donate electrophilic hydrogen. Materials which contain hydroaromatic compounds, and which therefore can be used as hydrogen donors in the invented method include, but are not limited to, partially hydrogenated coal fraction and partially hydrogenated petroleum fraction, and the distillates of such fractions. In addition, more pure hydroaromatic compounds can be utilized, including, but not limited to the classic hydroaromatic compounds of dihydrophenanthrene, tetrahydronaphthalene, hexahydropyrene, and combinations thereof.

One of the more salient advantages of this system is the efficient conversion of toxic polyaromatic compounds at low pressures of between approximately 1 atmosphere (atm) and 10 atm (particularly when hydroaromatics are used as hydrogen donors), and at temperatures ranging from between approximately 350° C. to 430° C.. As with temperature, a wide range of pressures can be utilized depending on reaction conditions. The sealed tube systems utilized in the examples yield good results at pressures ranging from approximately 1 atm to 10 atm, and more specifically at pressures ranging from 1 atm. to 1.5 atm. However, the use of other reactants (such as hydrogen gas as the hydrogen donor), or the implementation of a continuous process over a catalyst bed, would allow the system to operate at pressures ranging from 50 atm to 250 atm. The utilization of high hydrogen pressures would result in just as efficient conversions, as those obtained when using hydrogen donor at low pressures.

EXAMPLE 1

Three samples containing approximately 2.5 mg BP2000, 100 mg 9,10-dihydrophenanthrene and 100 mg of 10:1 (mol:mol) 1-chloronaphthalene and m-xylene (internal standard) were sealed and heated to different temperatures for 1 hour each. The weight ratio of haloaromatic to H-donor to catalyst was 1:1:0.025. The following conversions and selectivities were obtained:

| Temp. °C. | Conversion % | Selectivity % | | |
|---|---|---|---|---|
| | | Tetralin | Naphthalene | Chloro-Tetralin |
| 400 | 14 | 17 | 83 | 0 |
| 410 | 19 | 18 | 73 | 9 |
| 420 | 28 | 16 | 62 | 22 |
| 430 | 27 | 16 | 77 | 8 |

Mass balance exceeded 95% in all cases.

EXAMPLE 2 example 2 is a comparative example viz. example 1, wherein the reaction and products depicted in example 2 were obtained without utilization of a carbon catalyst. Three reaction tubes containing 100 mg 9,10-dihydrophenanthrene and 100 mg of 10:1 (mol:mol) 1-chloronaphthalene and m-xylene (internal standard) were sealed and heated to different temperatures for 1 hour each. Therefore, the weight ratio between the substrate and the H-donor was 1:1. The following conversions and selectivities were obtained:

| Temp. °C. | Conversion % | Selectivity % | | |
|---|---|---|---|---|
| | | Tetralin | Naphthalene | Chloro-Tetralin |
| 400 | 4 | 5 | 74 | 18 |
| 410 | 4 | 7 | 79 | 14 |
| 420 | 10 | 10 | 77 | 13 |
| 430 | 11 | 6 | 77 | 17 |

EXAMPLE 3

Three samples containing approximately 2.5 mg BP2000, 100 mg 9,10-dihydrophenanthrene and 100 mg of 10:1 (mol:mol)1-bromonaphthalene and m-xylene (internal standard) were sealed and heated to different temperatures for 1 hour each (weight ratio=1:1:0.025). The following conversions and selectivities were obtained:

| Temp. °C. | Conversion % | Selectivity % | | |
|---|---|---|---|---|
| | | Tetralin | Naphthalene | Bromo-Tetralin |
| 350 | 11 | 16 | 53 | 31 |
| 380 | 41 | 27 | 42 | 31 |
| 400 | 50 | 22 | 54 | 24 |
| 410 | 54 | 19 | 62 | 19 |

In all cases, mass balance exceeded 95%.

EXAMPLE 4 example 4 represents comparative data to example 3 wherein example 4 does not include the use of carbon molecular sieves as reduction catalysts. Three reaction tubes containing 100 mg 9,10 dihydrophenanthrene and 100 mg of 10:1 (mol:mol) 1-bromonaphthalene and m-xylene (internal standard) were sealed and heated to different temperatures for 1 hour each (weight ratio of 1:1). The following conversions and selectivities were obtained:

| Temp. °C. | Conversion % | Selectivity % | | |
|---|---|---|---|---|
| | | Tetralin | Naphthalene | Bromo-Tetralin |
| 350 | 0 | — | — | — |
| 380 | 6 | 8 | 68 | 24 |

-continued

| Temp. °C. | Conversion % | Selectivity % | | |
|---|---|---|---|---|
| | | Tetralin | Naphthalene | Bromo-Tetralin |
| 400 | 13 | 4 | 73 | 23 |
| 410 | 16 | 5 | 70 | 25 |

EXAMPLE 5

In example 5, a series of glass reaction tubes, each containing 2.5 mg BP2000, 25 mg 1-chloronaphthalene and 100 mg 9, 10-dihydrophenanthrene, were sealed and heated to various temperatures for one hour (weight ratio=1:4:0.1). Conversion and selectivities for each reaction is listed below:

| Temp. °C. | Conversion % | Selectivity % | | |
|---|---|---|---|---|
| | | Tetralin | Naphthalene | Chloro-Tetralin |
| 400 | 36 | 20 | 51 | 29 |
| 430 | 48 | 24 | 50 | 26 |

EXAMPLE 6

Example 6 is a comparative reaction sequence to example 5 wherein example 6 does not utilize carbon black catalyst. A series of reaction tubes containing 25 mg 1-chloronaphthalene and 100 mg 9,10-dihydrophenanthrene were heated to various temperatures for 1 hour (weight ratio=1:4). The products of this reaction sequence are listed below:

| Temp. °C. | Conversion % | Selectivity % | | |
|---|---|---|---|---|
| | | Tetralin | Naphthalene | Chloro-Tetralin |
| 400 | 6 | 9 | 69 | 20 |
| 430 | 16 | 10 | 65 | 25 |

EXAMPLE 7

The method of example 5 was repeated (at 400° C. only) with the exception of using a weight ratio of 1:10:0.1 for 1-chloronaphthalene to 9,10-dihydrophenanthrene to BP2000. Conversion of chloronaphthalene was 31% with selectivity of 25% tetralin, 42% naphthalene and 34% chlorotetralin.

EXAMPLE 8

The method of example 6 was repeated (at 400° C. only) using 1:10 chloronaphthalene to DHP weight ratio. Conversion was 6% with 71% selectivity to naphthalene and 29% chlorotetralin. No tetralin was produced.

EXAMPLE 9

The method of example 5 was repeated with the exceptions of using 1-bromonaphthalene as the halogenated reactant (1:4:0.1 weight ratio) and performing the experiments in a different temperature range. The product distributions are listed below:

| Temp. °C. | Conversion % | Selectivity % | | |
|---|---|---|---|---|
| | | Tetralin | Naphthalene | Bromo-Tetralin |
| 350 | 29 | 18 | 56 | 26 |
| 400 | 68 | 33 | 44 | 24 |
| 410 | 64 | 33 | 40 | 27 |

EXAMPLE 10

The method of example 9 was repeated without the presence of BP2000 (weight ratio=1:4). The results are tabulated below:

| Temp. °C. | Conversion % | Selectivity % | | |
|---|---|---|---|---|
| | | Tetralin | Naphthalene | Bromo-Tetralin |
| 350 | 0 | — | — | — |
| 400 | 8 | 0 | 63 | 37 |
| 410 | 23 | 10 | 59 | 31 |

EXAMPLE 11

A reaction tube containing approximately 2.5 mg BP2000, 25 mg 4-chlorobiphenyl and 100 mg 9,10-dihydrophenanthrene was heated to 400° C. for one hour (weight ratio=1:4:0.1). Conversion of the chlorobiphenyl was 5% with 73% selectivity to biphenyl obtained.

EXAMPLE 12

The method of example 11 was repeated in the absence of BP2000; 2% conversion was observed with 37% selectivity to biphenyl.

EXAMPLE 13

A reaction tube containing approximately 2.5 mg BP2000, 25 mg 9-bromophenanthrene and 100 mg 1,2,3,4-tetrahydronaphthalene was heated to 400° C. for one hour (weight ratio=1:4:0.1). Conversion of the bromophenanthrene was 95%, with 76% selectivity to phenanthrene, 14% to dihydrophenanthrene and 10% to polyhydrogenated ($H_2+$)phenanthrenes.

EXAMPLE 14

The method of example 13 was repeated in absence of BP2000. Twenty percent conversion was observed with 64% phenanthrene selectivity, 2% dihydrophenanthrene, 3% polyhydrogenated phenanthrenes and 31% for an unknown product, probably bromodihydrophenanthrene.

EXAMPLE 15

The method of example 9 was repeated (400° C. only) with the exception of using Ashland carbon fiber ACN-210-20 as the catalyst. Conversion of bromonaphthalene was 67%, with 23% tetralin, 61% naphthalene and 16% bromotetralin produced. Example 15 demonstrates the applicability of different carbon materials in hydrodehalogenation of polycondensed aromatics.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for dehalogenating halogenated polyaromatic compounds without incinerating the polyaromatic compounds but allowing the dehalogenated polyaromatic compound to be recovered and recycled, comprising:
   a) mixing the halogenated polyaromatic compounds with a hydrogen donor solvent and a carbon molecular sieve catalyst in a weight ratio of approximately 1:4:0.1, said catalyst selected from the group carbon molecular sieves consisting of carbon black and carbon fiber compounds;
   b) initiating a dehalogenation reaction in a liquid phase by heating the mixture to between approximately 330° C. and 450° C. for approximately one hour; and
   c) recovering the dehalogenated polyaromatic compounds.

2. The method as recited in claim 1 wherein the halogenated polyaromatic compounds are selected from the group consisting of halogenated biphenyls, halogenated condensed polyaromatic compounds and combinations thereof.

3. The method as recited in claim 1 wherein the halogenated polyaromatic compounds are selected from the group consisting of bromonaphthalene, chloronaphthalene, bromophenanthrene, chlorophenanthrene, chlorobiphenyl, bromobiphenyl, polybrominated naphthalene, polychlorinated naphthalene, polybrominated phenanthrene, polychlorinated phenanthrene, polychlorinated biphenyl, polybrominated biphenyl, and combinations thereof.

4. The method as recited in claim 1 wherein the hydrogen donor is selected from the group consisting of a hydroaromatic compound, a partially hydrogenated petroleum fraction, a partially hydrogenated coal fraction, and combinations thereof.

5. The method as recited in claim 4 wherein the dehalogenation reaction is carried out at pressures between approximately 1 atm and 10 atm.

6. The method as recited in claim 1 wherein the hydrogen donor is pressurized hydrogen gas and the reaction is carried out at a pressure selected from between approximately 50 atm to 250 atm.

7. A method for dehalogenating halogenated polyaromatic compounds without incinerating the polyaromatic compounds but allowing the dehalogenated polyaromatic compound to be recovered and recycled, comprising:
   a) mixing the halogenated polyaromatic compounds with a hydrogen donor solvent and a carbon molecular sieve catalyst in a weight ratio of 1:1:0.025, said catalyst selected from the group carbon molecular sieves consisting of carbon black and carbon fiber compounds;
   b) maintaining the mixture at a pressure of between 1 atm and 10 atm;
   c) initiating a dehalogenation reaction in a liquid phase by heating the mixture to a temperature selected from a range of approximately 350° C. to 450° C. for approximately 1 hour; and
   d) recovering the dehalogenated polyaromatic compounds.

8. The method as recited in claim 7 wherein the halogenated polyaromatic compounds are selected from the group consisting of halogenated biphenyls, halogenated condensed polyaromatic compounds and combinations thereof.

9. The method as recited in claim 7 wherein the hydrogen donor solvent is selected from the group consisting of a hydroaromatic compound, a partially hydrogenated petroleum fraction, a partially hydrogenated coal fraction, and combinations thereof.

10. The method as recited in claim 7 wherein the halogenated polyaromatic compounds are selected from the group consisting of bromonaphthalene, chloronaphthalene, bromophenanthrene, chlorophenanthrene, chlorobiphenyl, bromobiphenyl, polybrominated naphthalene, polychlorinated naphthalene, polybrominated phenanthrene, polychlorinated phenanthrene, polychlorinated biphenyl, polybrominated biphenyl, and combinations thereof.

11. A method for completely dehalogenating halogenated polyaromatic compounds without incinerating the polyaromatic compounds but allowing the dehalogenated polyaromatic compound to be recovered and recycled, comprising:
   a) mixing the halogenated polyaromatic compounds with a hydrogen donor solvent and a carbon black catalyst in a weight ratio of approximately 1:10:0.1;
   b) maintaining the mixture at between 1 atm and 10 atm; and
   c) initiating a dehalogenation reaction in a liquid phase by heating the mixture to approximately 400° C. for approximately 1 hour; and
   d) recovering the dehalogenated polyaromatic compounds.

12. The method as recited in claim 11 wherein the halogenated polyaromatic compounds are selected from the group consisting of halogenated biphenyls, halogenated condensed polyaromatic compounds and combinations thereof.

13. The method as recited in claim 11 wherein the hydrogen donor solvent is selected from the group consisting of a hydroaromatic compound, a partially hydrogenated petroleum fraction, partially hydrogenated coal fraction, and combinations thereof.

14. The method as recited in claim 11 wherein the halogenated polyaromatic compounds are selected from the group consisting of bromonaphthalene, chloronaphthalene, bromophenanthrene, chlorophenanthrene, chlorobiphenyl, bromobiphenyl, polybrominated naphthalene, polychlorinated naphthalene, polybrominated phenanthrene, polychlorinated phenanthrene, polychlorinated biphenyl, polybrominated biphenyl, and combinations thereof.

15. The method as recited in claim 11 wherein the hydrogen donor solvent is said recovered polyaromatic compound.

* * * * *